US008632814B2

(12) United States Patent
Brueck

(10) Patent No.: US 8,632,814 B2
(45) Date of Patent: Jan. 21, 2014

(54) SUBSTRATES COMPRISING SWITCHABLE FERROMAGNETIC NANOPARTICLES

(75) Inventor: Ekkehard Brueck, Delft (NL)

(73) Assignee: BASF SE, Ludwigshafen (DE)

( * ) Notice: Subject to any disclaimer, the term of this patent is extended or adjusted under 35 U.S.C. 154(b) by 351 days.

(21) Appl. No.: 12/887,138

(22) Filed: Sep. 21, 2010

(65) Prior Publication Data

US 2011/0070620 A1   Mar. 24, 2011

(30) Foreign Application Priority Data

Sep. 21, 2009 (EP) .................... 09170811

(51) Int. Cl.
*A61K 9/14* (2006.01)
(52) U.S. Cl.
USPC .......................................... 424/489; 424/9.32
(58) Field of Classification Search
None
See application file for complete search history.

(56) References Cited

U.S. PATENT DOCUMENTS

2005/0249817 A1* 11/2005 Haik et al. ................... 424/617
2009/0258073 A1  10/2009 Tishin et al.

FOREIGN PATENT DOCUMENTS

| EP | 1 897 590 A1 | 3/2008 |
|---|---|---|
| WO | WO 2004/068512 A1 | 8/2004 |
| WO | WO 2008/044963 A2 | 4/2008 |
| WO | WO 2008/044963 A3 | 4/2008 |

OTHER PUBLICATIONS

Jain et al. Molecular Pharmaceutics 2(3), p. 194-205, 2005.*
Hudl et al. Condensed Matter, arXiv:0904.2256v1, Apr. 15, 2009.*
Wang et al. Applied Physics Letters, 98, 083107, 2011.*
U.S. Appl. No. 13/044,977, filed Mar. 10, 2011, Brueck, et al.
D. T. Cam Thanh, et al., "Magnetocaloric Effect in MnFe(P,Si,Ge) Compounds", Journal of Applied Physics 99, 08Q107, 2006, 3 pages.
Zhongmin Wang, et al., "Structural Stability of Single-Layered $LaNi_{4.25}Al_{0.75}$ Film and its Electrochemical Hydrogen-Storage Properties", Rare Metals, A Chinese Journal of Science, Technology & Applications in the Field of Rare Metals, vol. 25, No. 5, Oct. 2006, pp. 543-548.
U.S. Appl. No. 12/990,094, filed Oct. 28, 2010, Degen, et al.
U.S. Appl. No. 12/989,020, filed Oct. 21, 2010, Brueck, et al.
International Search Report issued Dec. 17, 2010, in Patent Application No. PCT/EP2010/063733 (with English Translation of Category of Cited Documents in the attached foreign language Search Report).
W. Dagula, et al., "Magnetic-Entropy Change in $Mn_{1.1}Fe_{0.9}P_{1-x}Ge_x$ Compounds", IEEE Transactions on Magnetics, vol. 41, No. 10, XP 11140646, Oct. 1, 2005, pp. 2778-2780.
D. T. Cam Thanh, et al., Structure, magnetism, and magnetocaloric properties of $MnFeP_{1-x}Si_x$ compounds, Journal of Applied Physics, vol. 103, No. 7, 07B318, XP 002611165, Jan. 31, 2008, pp. 1-3.

* cited by examiner

*Primary Examiner* — Nissa Westerberg
(74) *Attorney, Agent, or Firm* — Oblon, Spivak, McClelland, Maier & Neustadt, L.L.P.

(57) ABSTRACT

In a process for producing organic substrate particles bonded to switchable ferromagnetic nanoparticles with a mean particle diameter in the range from 10 to 1000 nm, the ferromagnetic nanoparticles used are those nanoparticles which are nonferromagnetic at first, but become ferromagnetic when the temperature is lowered, these at first nonferromagnetic nanoparticles in dispersed form are bonded to the organic substance particles, and then the nanoparticles bonded to the substrate particles are made ferromagnetic as a result of the temperature being lowered.

20 Claims, 1 Drawing Sheet

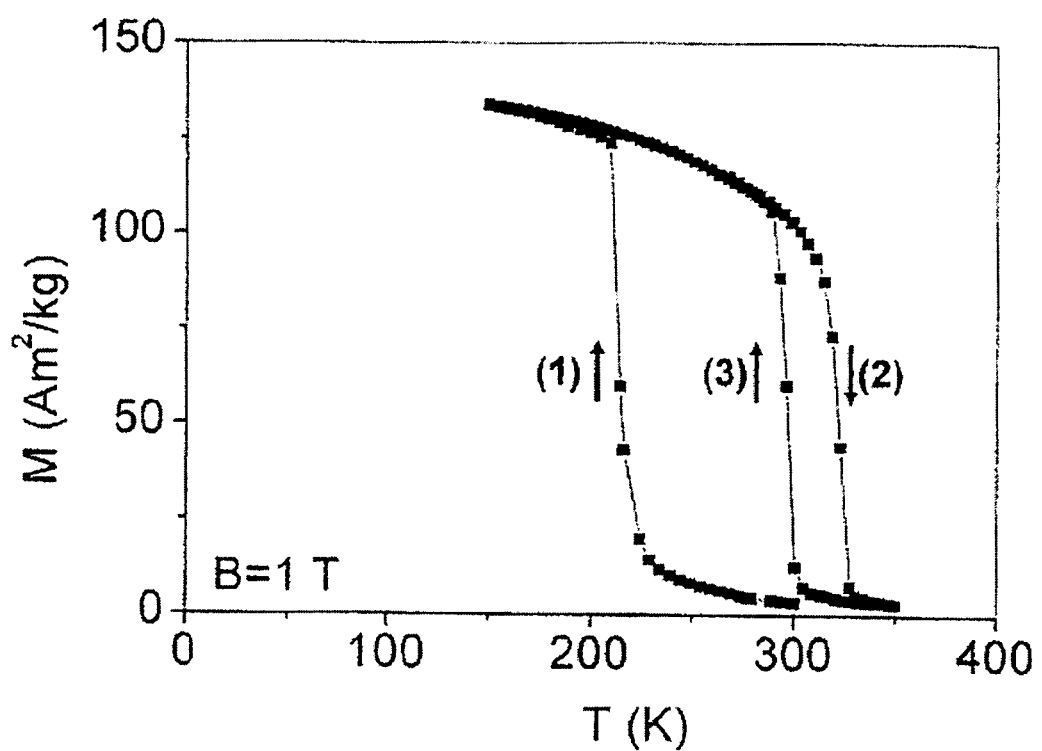

SUBSTRATES COMPRISING SWITCHABLE FERROMAGNETIC NANOPARTICLES

The invention relates to processes for producing organic substrate particles bonded to switchable ferromagnetic nanoparticles, to corresponding diagnostic substrate particles and to the use of such nanoparticles for hyperthermia treatment.

In the context of the invention, the expression "ferromagnetic" is understood to mean both "ferromagnetic" and "magnetic".

At present, magnetic particles already have various uses for labeling and manipulation of biological objects. Magnetic particles coupled to antibodies are used, for example, for the magnetic diagnosis of disorders. A problem in the production of such small particles in the nanometer range is the tendency of the magnetic particles to form lumps or aggregates. This complicates the homogeneous attachment of the antibodies to the magnetic particles, and the particle size increases significantly in an undesired manner.

Magnetic particles such as $Fe_3O_4$ colloids are used, for example, for hyperthermia treatment, especially in cancer therapy. Hyperthermia is a type of cancer treatment in which body tissue is exposed to high temperatures of up to 45° C. It has been found that high temperatures can damage and kill cancer cells, typically with only minor side effects on normal tissue. By killing cancer cells and destroying the cell structure, hyperthermia can be used to reduce the size of tumors. In this context, it is desirable to use magnetic particles with better suitability, which can likewise be heated in the human body by radio waves.

Additionally known is the bonding of substances with magnetocaloric properties such as $MnFeP_{0.35}As_{0.65}$ and MnAs to polymeric carriers for active pharmacological ingredients. WO 2008/044963 describes such bound carrier particles, in which heating of the magnetocaloric materials can alter the release properties of the associated polymer matrix for the active pharmacological ingredient, such that the active ingredient can be released in a controlled manner.

It is an object of the present invention to provide an improved process for producing organic substrate particles bonded to switchable ferromagnetic nanoparticles, which are usable especially as biomarkers, biosensors, hyperthermia active ingredients or pharmaceutical carrier materials.

The object is achieved in accordance with the invention by a process for producing organic substrate particles bonded to switchable ferromagnetic nanoparticles with a mean particle diameter in the range from 10 to 1000 nm, wherein the ferromagnetic nanoparticles used are those nanoparticles which are nonferromagnetic at first, but become ferromagnetic when the temperature is lowered, these at first nonferromagnetic nanoparticles in dispersed form are bonded to the organic substance particles, and then the nanoparticles bonded to the substrate particles become ferromagnetic as a result of the temperature being lowered.

The object is also achieved by diagnostic substrate particles which comprise organic substrate particles bonded to switchable ferromagnetic nanoparticles with a mean particle diameter in the range from 10 to 1000 nm, said substrate particles having a specific bonding action for a substance to be analyzed.

The object is additionally achieved by the use of switchable ferromagnetic nanoparticles which become ferromagnetic when the temperature is lowered for producing a medicament for hyperthermia treatment in the human or animal body.

The object is additionally achieved by a medicament for hyperthermia treatment in the human or animal body, comprising switchable ferromagnetic nanoparticles with a mean particle diameter in the range from 10 to 1000 nm, which become ferromagnetic when the temperature is lowered.

BRIEF DESCRIPTION OF THE DRAWINGS

FIG. 1 shows the temperature dependence of the magnetization of $MnFeP_{0.50}Si_{0.50}$.

It has been found in accordance with the invention that switchable ferromagnetic nanoparticles can be used in a suitable manner for producing biomarkers, biosensors, hyperthermia active ingredients or pharmaceutical carrier materials. "Switchable" ferromagnetic nanoparticles are understood to mean those which are nonferromagnetic at first but become ferromagnetic when the temperature is lowered. After the production of the nanoparticles from the starting materials, they are nonferromagnetic at first and only become ferromagnetic when cooled. The nanoparticles are preferably at first nonferromagnetic at ambient temperature (22° C.) and become ferromagnetic when the temperature is lowered to values below room temperature.

"Nanoparticles" are understood to mean those particles which have a mean particle diameter in the range from 10 to 1000 nm, preferably 20 to 500 nm, especially 50 to 200 nm. The mean particle diameter is preferably determined by laser light scattering or electron microscopy. It is preferably the weight-average particle diameter. The lower limit of the particle size results from the fact that the particles must still be ferromagnetic at ambient temperature or use temperature. This is typically still the case for a minimum particle diameter of 10 nm.

To produce the substrate particles, the at first nonferromagnetic nanoparticles are typically introduced into a dispersion, for example an aqueous or water-based dispersion, and bonded to the organic substrate particles in the dispersed form. Since the nanoparticles are nonferromagnetic at this time, an agglomeration of the particles and hence an increase in the mean particle size can reliably be prevented. This dispersion can be used later, for example, for hyperthermia treatment.

Useful organic substrate particles include any suitable substrate particles which impart the desired effect. The organic substrate particles must have suitable anchor groups which allow bonding to the ferromagnetic nanoparticles. It may be possible, for example, that the organic substrate particles are applied as a coating or shell to the ferromagnetic nanoparticles. Other attachments are also possible and are known to those skilled in the art. The organic substrate particles may be selected from a wide range of suitable substrate particles. Biomarkers are for example, antibodies or biological or organic-synthetic substances which enter into interactions with other substances at a later stage. For example, ferromagnetic nanoparticles can be bonded to antibodies which in turn enter into bonds with antigens in order thus to obtain biomarkers or biosensors. Particles coupled to particular antibodies are utilized, for example, for magnetic diagnoses of disorders. For a quantitative diagnosis, it is important to be able to use the ferromagnetic nanoparticles with a minimum variation in the particle size, since the proportion of the ferromagnetic nanoparticles is ultimately counted.

Biomarkers can be used, for example, in environmental analysis, in the analysis of water and blood, for example for proteins, carbohydrates or hormones.

Biosensors may serve to detect any biological ingredients, for example in liquids or gas streams. In this case, the organic substrate particles have bonding sites to the substances to be analyzed or to be quantified. For the recognition of the substances to be determined, biosensors utilize biological systems at different levels of integration. Such biological systems may, for example, be antibodies, enzymes, organelles or microorganisms. The immobilized biological system of the biosensor interacts with the analyte. This results in physicochemical changes. The determination of glucose in the blood during and after operations is enabled by applying the glucose oxidase enzyme. The areas of use for biosensors in the analysis of water and wastewater can be divided into biosensors for determination of single components, biosensors for determination of toxicity and mutagenicity, and biosensors for determining biochemical oxygen demand (BOD). The bacteria content of bathing waters or of wastewaters can be determined by means of a biosensor.

The penicillin concentration in a bioreactor in which fungal strains are cultivated can be determined with a biosensor. The biological component of the sensor used here is the enzyme acylase.

The organic substrate particles may also be pharmaceutical carrier materials which take up active pharmacological ingredients. Such organic polymer substrate particles are described, for example, in WO 2008/044963. Reference should be made especially to page 16 line 18 to page 17 line 11 of this document.

Bioactive compounds which can be bonded to the substrate particles are, for example, antigens, antibodies, nucleotides, gel formers, enzymes, bacteria, yeasts, fungi, viruses, polysaccharides, lipids, proteins, hormones, hydrocarbons and cell material. These can be used as biosensor materials. For a further description, reference may be made to WO 2008/044963, especially page 17.

Biosensors (biochips) are used typically in compositions of sensors for bioanalytic applications in biotechnology. Examples are immunoassays, which are used widely in clinical diagnosis for detection of disorders or physiological states. For a description of the biosensors, reference may be made to WO 2008/044963, page 17 line 25 to page 18 line 17.

The biomarkers and biosensors are used especially for quantitative determination or concentration measurement of active biological ingredients.

The ultimately obtained organic substrate particles bonded to the ferromagnetic nanoparticles have an overall mean particle diameter in the range from preferably 1.1 to 5 times, more preferably 1.2 to 2 times, the diameter of the magnetocaloric particles.

Preferably, the switchable ferromagnetic nanoparticles are at first nonferromagnetic at temperatures of 22° C. or higher and become ferromagnetic as a result of cooling to temperatures of less than 22° C.

Preferably, the switchable ferromagnetic nanoparticles exhibit a virgin effect, such that, when the at first nonferromagnetic nanoparticles are first cooled, the critical temperature of the transition to the ferromagnetic state (critical temperature 1) is lower than for subsequent reheating and cooling (critical temperature 2).

The critical temperature 1 is passed through only in the course of the first cooling, whereas the critical temperature 2 is passed through in the course of the subsequent heating/cooling cycles. The critical temperature 1 is preferably below 22° C., preferably <0° C., particularly <−15° C., especially <−25° C., and the critical temperature 2 is above 22° C., for example body temperature±2° C.

The switchable ferromagnetic nanoparticles may be selected from all suitable nanoparticles. The switchable ferromagnetic nanoparticles preferably comprise Mn and additionally Fe and/or As, and preferably have the $Fe_2P$ structure or Na—Zn-13 structure. Alternatively, they may comprise La, Fe and Si.

More preferably, the switchable ferromagnetic nanoparticle material comprises MnFe(P/As, Si/Ge) with $Fe_2P$ structure or MnAs with or without Cu and/or Fe as dopants, or LaFeSiH.

The notation "P/As" and "Si/Ge" means that, in each case, phosphorus, arsenic or phosphorus and arsenic, and silicon, germanium or silicon and germanium, may respectively be present.

Suitable compositions are also described in WO 2008/044963.

The switchable ferromagnetic nanoparticles preferably exhibit magnetocaloric properties. The nanoparticles preferably exhibit a hysteresis and adiabatic temperature change of 2 to 6 K/tesla, for example about 4 K/tesla of field strength. The hysteresis is preferably at least 5 K.

The ferromagnetic or thermomagnetic materials used in accordance with the invention can be produced in any suitable manner.

The ferromagnetic or thermomagnetic materials are produced, for example, by solid phase reaction of the starting elements or starting alloys for the material in a ball mill, subsequent pressing, sintering and heat treatment under inert gas atmosphere and subsequent slow cooling to room temperature. Such a process is described, for example, in J. Appl. Phys. 99, 2006, 08Q107.

Processing by means of melt-spinning is also possible. This makes possible a more homogeneous element distribution which leads to an improved magnetocaloric effect; cf. Rare Metals, Vol. 25, October 2006, pages 544 to 549. In the process described there, the starting elements are first induction-melted in an argon gas atmosphere and then sprayed in the molten state through a nozzle onto a rotating copper roller. This is followed by sintering at 1000° C. and slow cooling to room temperature.

In addition, reference may be made to WO 2004/068512 for the preparation.

The materials obtained by these processes frequently exhibit large thermal hysteresis. For example, in compounds of the $Fe_2P$ type substituted by germanium or silicon, large values for the thermal hysteresis in a wide range of 10 K or more are observed.

Materials used in accordance with the invention preferably exhibit a hysteresis of at least 5 K, more preferably of at least 6.5 K, preferably in a temperature range between body temperature and above 42° C.

Preference is given to a process for producing ferromagnetic or thermomagnetic materials, comprising the following steps:
a) reacting chemical elements and/or alloys in a stoichiometry which corresponds to the metal-based material in the solid and/or liquid phase,
b) if appropriate converting the reaction product from stage a) to a solid,
c) sintering and/or heat treating the solid from stage a) or b),
d) cooling the sintered and/or heat-treated solid from stage c).

The thermal hysteresis can be established and a large magnetocaloric effect can be achieved when the metal-based materials are cooled quickly or slowly to ambient temperature after the sintering and/or heat treatment.

In step (a) of the process, the elements and/or alloys which are present in the later ferromagnetic or thermomagnetic material are reacted in a stoichiometry which corresponds to the ferromagnetic or thermomagnetic material in the solid or liquid phase.

Preference is given to performing the reaction in stage a) by combined heating of the elements and/or alloys in a closed vessel or in an extruder, or by solid phase reaction in a ball mill. Particular preference is given to performing a solid phase reaction, which is effected especially in a ball mill. Such a reaction is known in principle; cf. the documents cited above. Typically, powders of the individual elements or powders of alloys of two or more of the individual elements which are present in the later ferromagnetic or thermomagnetic material are mixed in pulverulent form in suitable proportions by weight. If necessary, the mixture can additionally be ground in order to obtain a microcrystalline powder mixture. This powder mixture is preferably heated in a ball mill, which leads to further comminution and also good mixing, and to a solid phase reaction in the powder mixture. Alternatively, the individual elements are mixed as a powder in the selected stoichiometry and then melted.

The combined heating in a closed vessel allows the fixing of volatile elements and control of the stoichiometry. Specifically in the case of use of phosphorus, this would evaporate easily in an open system.

The reaction is followed by sintering and/or heat treatment of the solid, for which one or more intermediate steps can be provided. For example, the solid obtained in stage a) can be pressed before it is sintered and/or heat treated. This allows the density of the material to be increased, such that a high density of the thermomagnetic material is present in the later application. Pressing is known per se and can be carried out with or without pressing aids. It is possible to use any suitable mold for pressing. By virtue of the pressing, it is already possible to obtain shaped bodies in the desired three-dimensional structure. The pressing may be followed by the sintering and/or heat treatment of stage c), followed by the cooling or quenching of stage d).

To produce the nanoparticles, grinding may follow.

Alternatively, it is possible to send the solid obtained from the ball mill to a melt-spinning process. Melt-spinning processes are known per se and are described, for example, in Rare Metals, Vol. 25, October 2006, pages 544 to 549, and also in WO 2004/068512.

The melt-spinning achieves a high processing rate, since the subsequent sintering and heat treatment can be shortened. Specifically on the industrial scale, the production of the ferromagnetic or thermomagnetic materials thus becomes significantly more economically viable. Spray-drying also leads to a high processing rate, especially because the desired particle size can be established easily.

The cooling should not be too rapid, in order to obtain sufficiently high hysteresis values.

Alternatively, in stage b), spray cooling can be carried out, in which a melt of the composition from stage a) is sprayed into a spray tower. The spray tower may, for example, additionally be cooled. In spray towers, cooling rates in the range from $10^3$ to $10^5$ K/s, especially about $10^4$ K/s, are frequently achieved. The spray cooling can be effected in an electrical field, in order to obtain monodisperse particles.

The sintering and/or heat treatment of the solid is effected in stage c) preferably first at a temperature in the range from 500 to 1800° C. for sintering and then at a lower temperature for heat treatment. These values apply especially to powders. The sintering is performed preferably for a period of from 1 to 50 hours, more preferably from 2 to 20 hours, especially from 5 to 15 hours. The heat treatment is performed preferably for a period in the range from 10 to 100 hours, more preferably from 10 to 60 hours, especially from 30 to 50 hours. The exact periods can be adjusted to the practical requirements according to the materials.

In the case of use of the melt-spinning process, the period for sintering or heat treatment can be shortened significantly, for example to periods of from 5 minutes to 5 hours, preferably from 10 minutes to 1 hour. Compared to the otherwise customary values of 10 hours for sintering and 50 hours for heat treatment, this results in a major time advantage.

The sintering/heat treatment results in partial melting of the particle boundaries, such that the material is compacted further.

The melting and rapid or slow cooling in stage b) thus allows the duration of stage c) to be reduced considerably. This also allows continuous production of the ferromagnetic or thermomagnetic materials.

Particular preference is given in accordance with the invention to the process sequence of
a) solid phase reaction of chemical elements and/or alloys in a stoichiometry which corresponds to the ferromagnetic or thermomagnetic material in a ball mill,
b) melt spinning or shaping the material obtained in stage a),
c) heat treating the solid from stage b) at a temperature in the range from 430 to 1200° C., preferably from 800 to 1000° C., for a period of from 10 seconds or 1 minute to 5 hours, preferably from 30 minutes to 2 hours,
d) quenching or cooling the heat treated solid from stage c).

Alternatively, in stage c), the resulting ribbons can be ground to a powder.

The particle size of the ferromagnetic nanoparticles is preferably determined by laser light scattering, as described.

Preferably in accordance with the invention, the switchable ferromagnetic nanoparticles which become ferromagnetic when the temperature is lowered are used to produce a medicament for hyperthermia treatment of the human or animal body. These nanoparticles are preferably magnetocaloric. The hyperthermia treatment serves especially for cancer treatment, as already detailed at the outset.

The invention also relates to a medicament for hyperthermia treatment of the human or animal body, comprising the switchable ferromagnetic nanoparticles described, which become ferromagnetic when the temperature is lowered.

The particles preferably become ferromagnetic in the course of cooling. Specifically in the case of treatment of cancer, the nanoparticles should be ferromagnetic within a temperature range from 37 to 42° C. At higher temperatures or preferably a maximum temperature of 42° C., they can lose their ferromagnetic behavior in one embodiment of the invention. The result is that the hysteresis is switched off in the case of overheating, such that the substances lose their ferromagnetic character and can simply be excreted from the body.

This thermal switchoff should occur at higher temperatures than the temperatures at which cancer is destroyed.

It is important especially for all applications that the ferromagnetic nanoparticles are ferromagnetic at ambient temperature (22° C.) or at the use temperature.

A preferred material used is MnFe(P,Si), which exhibits the unexpected property that it is nonmagnetic after production at room temperature (22° C.). Only after it is cooled briefly a few degrees below a particular critical temperature is it ferromagnetic at room temperature and higher. The corresponding properties are shown in the appended FIGURE, FIG. 1. The FIGURE shows the temperature dependence of the magnetization of $MnFeP_{0.50}Si_{0.50}$. The curve (1) shows the virgin effect, i.e. the behavior in the course of the first cooling. The curve (2) shows the behavior in the course of the subsequent heating, (3) that in the course of the subsequent cooling. The hysteresis of the ferromagnetic material, which is significantly greater than 5 K, is very readily noticeable.

The nonmagnetic property at the start can considerably simplify the attachment of the antibodies, such that a magnetic biomarker is considerably simpler to produce than hitherto. For in vitro applications, biocompatibility is unimportant, and so a bond to any suitable organic substrate particles is possible. In the case of use in vivo, maximum compatibility of the organic substrate particles with the human or animal body should be ensured. In addition to hypothermic cancer treatment, the inventive particles can also be used as NMR contrast agents.

In the case of hyperthermia, it may additionally be beneficial that the material shown in the FIGURE, after it has been heated once above $T_2$, is no longer ferromagnetic and can thus be excreted in a simpler manner.

The invention is illustrated in detail by the examples which follow.

EXAMPLE 1

Evacuated quartz ampoules which comprised pressed samples of MnFePGe were kept at 1100° C. for 10 hours in order to sinter the powder. This sintering was followed by heat treatment at 650° C. for 60 hours, in order to bring about homogenization. This was followed by slow cooling in the oven to room temperature. The XRD patterns show that all samples crystallize in a structure of the $Fe_2P$ type. The following compositions were obtained:

$Mn_{1.1}Fe_{0.9}P_{0.81}Ge_{0.19}$, $Mn_{1.1}Fe_{0.9}P_{0.78}Ge_{0.22}$, $Mn_{1.1}Fe_{0.9}P_{0.75}Ge_{0.25}$ and $Mn_{1.2}Fe_{0.8}P_{0.81}Ge_{0.19}$. The values observed for the thermal hysteresis are more than 10 K for each of these samples. More rapid cooling can reduce the hysteresis.

The thermal hysteresis was determined in a magnetic field of 0.5 tesla.

The Curie temperature can be adjusted by varying the Mn/Fe ratio and the Ge concentration, as can the value for the thermal hysteresis.

The Curie temperature and the thermal hysteresis decrease with increasing Mn/Fe ratio. As a result, the MnFePGe compounds exhibit relatively large MCE values in low field.

EXAMPLE 2

The material $MnFeP_{0.50}Si_{0.50}$ was produced as described in example 1. The T dependence of the magnetization is shown in FIG. 1.

The invention claimed is:

1. A process for producing organic substrate particles, comprising bonding an organic substrate compound to switchable nanoparticles with a mean particle diameter in the range from 10 to 1000 nm,
wherein
the nanoparticles are in a nonferromagnetic state during said bonding and are nanoparticles that have not been switched to the ferromagnetic state by a first cooling of the nanoparticles prior to said bonding, and
said bonding is carried out in an aqueous dispersion.

2. The process according to claim 1, wherein the switchable ferromagnetic nanoparticles are at first nonferromagnetic at temperatures of 22° C. or higher and become ferromagnetic as a result of a first cooling to temperatures of less than 22° C.

3. The process according to claim 1, wherein the switchable ferromagnetic nanoparticles exhibit a virgin effect, such that, when the at first nonferromagnetic nanoparticles are first cooled, the critical temperature of the transition to the ferromagnetic state (critical temperature 1) is lower than for subsequent reheating and cooling (critical temperature 2).

4. The process according to claim 3, wherein the critical temperature 1 is below 22° C.

5. The process according to claim 1, wherein the organic substrate compound comprises at least one member selected from the group consisting of a biomarker, a biosensor, and a pharmaceutical carrier material.

6. The process according to claim 1, wherein the switchable nanoparticles comprise Mn and at least one of Fe and As.

7. The process according to claim 6, wherein the switchable ferromagnetic nanoparticles comprise LaFeSiH or MnFe(P/As, Si/Ge) having a $Fe_2P$ structure or MnAs with or without at least one of Cu and Fe as dopants.

8. The process according to claim 1, wherein the switchable ferromagnetic nanoparticles exhibit magnetocaloric properties.

9. The process according to claim 1, wherein the switchable nanoparticles comprise La, Fe and Si.

10. The process according to claim 1, wherein the switchable nanoparticles comprise Mn and at least one of Fe and As and has a $Fe_2P$ or Na—Zn-13 structure.

11. The process according to claim 1, wherein the switchable nanoparticles have a mean particle diameter in the range from 20 to 500 nm.

12. The process according to claim 1, wherein the switchable nanoparticles have a mean particle diameter in the range from 50 to 200 nm.

13. A process for producing organic substrate particles, comprising:
bonding an organic substrate compound to switchable nanoparticles with a mean particle diameter in the range from 10 to 1000 nm; and
cooling the nanoparticles, thereby obtaining ferromagnetic nanoparticles comprising said organic substrate bonded thereto,
wherein
the nanoparticles are in a nonferromagnetic state during said bonding and are nanoparticles that have not been switched to the ferromagnetic state by a first cooling of the nanoparticles prior to said bonding, and
said bonding is carried out in an aqueous dispersion.

14. The process according to claim 13, wherein the switchable ferromagnetic nanoparticles are at first nonferromagnetic at temperatures of 22° C. or higher and become ferromagnetic as a result of a first cooling to temperatures of less than 22° C.

15. The process according to claim 13, wherein the switchable ferromagnetic nanoparticles exhibit a virgin effect, such that, when the at first nonferromagnetic nanoparticles are first cooled, the critical temperature of the transition to the ferromagnetic state (critical temperature 1) is lower than for subsequent reheating and cooling (critical temperature 2).

16. The process according to claim 15, wherein the critical temperature 1 is below 22° C.

17. The process according to claim 13, wherein the organic substrate compound comprises at least one member selected from the group consisting of a biomarker, a biosensor, and a pharmaceutical carrier material.

18. The process according to claim 13, wherein the switchable nanoparticles comprise Mn and at least one of Fe and As.

19. The process according to claim 18, wherein the switchable ferromagnetic nanoparticles comprise LaFeSiH or MnFe(P/As, Si/Ge) having a $Fe_2P$ structure or MnAs with or without at least one of Cu and Fe as dopants.

20. The process according to claim 13, wherein the switchable ferromagnetic nanoparticles exhibit magnetocaloric properties.

\* \* \* \* \*